(12) United States Patent
Chen et al.

(10) Patent No.: US 8,739,623 B2
(45) Date of Patent: Jun. 3, 2014

(54) MOISTURE SENSORS ON CONDUCTIVE SUBSTRATES

(75) Inventors: Zhi David Chen, Lexington, KY (US); Ibrahim Yucedag, Duzce (TR)

(73) Assignee: The University of Kentucky Research Foundation, Lexinton, KY (US)

( * ) Notice: Subject to any disclaimer, the term of this patent is extended or adjusted under 35 U.S.C. 154(b) by 286 days.

(21) Appl. No.: 13/416,437

(22) Filed: Mar. 9, 2012

(65) Prior Publication Data

US 2013/0233073 A1    Sep. 12, 2013

(51) Int. Cl.
*G01N 27/22* (2006.01)
*H01H 9/28* (2006.01)

(52) U.S. Cl.
USPC ........................................ 73/335.04; 361/268

(58) Field of Classification Search
CPC ........................... G01N 27/223; G01N 27/225
USPC ........................................ 73/335.04; 361/268
See application file for complete search history.

(56) References Cited

U.S. PATENT DOCUMENTS

| | | | |
|---|---|---|---|
| 3,861,031 A | 1/1975 | Furuichi | |
| 3,987,676 A | 10/1976 | Bennewitz | |
| 4,057,823 A | 11/1977 | Burkhardt et al. | |
| 4,393,434 A | 7/1983 | Imai et al. | |
| 4,530,030 A * | 7/1985 | Woest et al. | 361/286 |
| 4,603,455 A * | 8/1986 | Woest et al. | 29/25.42 |
| 4,965,698 A * | 10/1990 | Thoma et al. | 361/286 |
| 5,001,453 A | 3/1991 | Ikejiri et al. | |
| 5,027,077 A | 6/1991 | Yanagisawa et al. | |
| 5,075,667 A | 12/1991 | Nishiwaki et al. | |
| 5,177,662 A * | 1/1993 | Thoma | 361/286 |
| 5,408,381 A * | 4/1995 | Thoma et al. | 361/286 |
| 5,493,897 A | 2/1996 | Nomura et al. | |
| 5,916,425 A | 6/1999 | Leader et al. | |
| 6,540,963 B2 | 4/2003 | Sugiyama | |
| 6,705,152 B2 | 3/2004 | Routkevitch et al. | |
| 7,181,966 B2 | 2/2007 | Isogai et al. | |
| 7,771,620 B2 | 8/2010 | Chung et al. | |
| 2004/0194546 A1 | 10/2004 | Kanehori | |
| 2009/0145220 A1 | 6/2009 | Langenbacher et al. | |

FOREIGN PATENT DOCUMENTS

| | | |
|---|---|---|
| DE | 2742902 A1 | 8/1978 |
| JP | 59159062 A | 9/1984 |
| JP | 60152946 A | 8/1985 |
| JP | 5010910 A | 1/1993 |

* cited by examiner

*Primary Examiner* — Hezron E Williams
*Assistant Examiner* — Nathaniel Kolb
(74) *Attorney, Agent, or Firm* — King & Schickli, PLLC

(57) ABSTRACT

A moisture sensor includes a first electrode (a conductive substrate) having a first sensor portion and a first terminal portion as well as a second electrode having a second sensor portion and a second terminal portion. The moisture sensor also includes a layer of porous dielectric material sandwiched between the first sensor portion and the second sensor portion. Further the moisture sensor includes a layer of dense insulating material sandwiched between the first terminal portion and the second terminal portion. Leads are then connected to the two terminal portions.

17 Claims, 1 Drawing Sheet

MOISTURE SENSORS ON CONDUCTIVE SUBSTRATES

This invention was made with at least partial government support under NSF contract No. ECS-0609064. The government may have certain rights in this invention.

TECHNICAL FIELD

This document relates to the field of electronic sensors and more particularly, to a new and improved moisture sensor and a method for making the same.

BACKGROUND SECTION

Moisture sensors are humidity-sensing capacitors. Various moisture sensors are known in the art including those found in U.S. Pat. Nos. 3,861,031, 5,075,667 and 5,027,077.

Typically moisture sensors have a porous alpha-$Al_2O_3$ film as a dielectric material with a conductive metal substrate as the bottom electrode and gold thin film as the top electrode. While conductive glues provide a simple and cost effective means for attaching a lead to an electrode it has not been possible to connect a lead to the top electrode using conductive glues in prior art sensor designs. More specifically, typical conductive glues and conductive pastes have to be avoided because they trap moisture when they are on the porous surface of the active sensing area. This trapped moisture significantly affects the sensors accuracy and response time for moisture levels of <−50° C. Dew Point.

Disclosed in this document is a new and improved moisture sensor having a structure that allows the lead to be connected to the top electrode with conductive glue or paste, which is away from the porous surface of the active sensing area and located on a dense insulating layer to improve the overall performance of the sensor.

SUMMARY SECTION

A moisture sensor comprises a first electrode (a conductive substrate) having a first sensor portion and a first terminal portion and a second electrode having a second sensor portion and a second terminal portion. The moisture sensor further includes a layer of porous sensing dielectric material sandwiched between the first sensor portion and the second sensor portion. In addition the moisture sensor includes a layer of dense insulating material sandwiched between the first terminal portion and the second terminal portion.

Still further describing the moisture sensor, a first lead is connected to the first terminal portion and a second lead is connected to the second terminal portion. A second lead is connected to the second terminal portion by a conductive adhesive. The first lead is connected to the first electrode in various ways.

Further describing the moisture sensor, the second electrode covers a step at a transition between the second sensor portion and the second terminal portion, which is created by depositing a layer of dense insulating material on the conductive substrate (first electrode). The first electrode is made from a conductive substrate, which is one of the following: metals, heavily doped semiconductors, and the combination, for examples, aluminum, heavily doped silicon, and the Al/Si combination. The second electrode is made from a material selected from the group consisting of a conductive metal film, a conductive metal alloy, a conductive metal film, a conductive metal alloy film, a platinum film, a palladium film and a gold/titanium film and a gold film. The layer of porous dielectric material is made from porous alumina. Still further the layer of dense insulating material is made from a material selected from a group consisting of silicon nitride, silicon oxynitride, aluminum oxide, hafnium oxide, hafnium silicon oxide, hafnium silicon oxynitride, silicon dioxide and mixtures thereof.

In one particularly useful embodiment the first electrode is made of aluminum, the second electrode is made from gold film, the layer of porous dielectric material is porous alpha-alumina and the layer of dense insulated material is dense silicon dioxide.

A method of manufacturing a moisture sensor of the type described is also provided. The method includes the steps of depositing a layer of dense insulating material on a first terminal portion of the first electrode (conductive substrate), providing a layer of porous dielectric material on a first sensor portion of the first electrode and depositing a second electrode over the layer of dense insulating material and layer of porous dielectric material so as to produce a sensor assembly. The second electrode of the sensor assembly has a second sensor portion overlying the layer of porous dielectric material and a second terminal portion overlying the layer of dense insulating material.

The method further includes a step of connecting a first lead to the first terminal portion and a second lead to the second terminal portion. Conductive adhesive is utilized to connect the second lead to the second terminal portion. A first lead is connected to the first terminal portion in one of the three ways: (1) a conductive fastener such as a conductive screw through an aperture across the layer of dense insulating material and the first terminal portion of the first electrode; (2) a conductive adhesive, where a small portion of the dense insulating material is etched off to expose the conductive first terminal portion to the conductive adhesive (no aperture is needed in this case); (3) a conductive adhesive directly connected to the first terminal portion from the bottom (no aperture is needed in this case).

In the following description there is shown and described a moisture sensor. As it should be realized, the moisture sensor is capable of other, different embodiments and its several details are capable of modification in various, obvious aspects. Accordingly, the drawings and descriptions will be regarded as illustrative in nature and not as restrictive.

BRIEF DESCRIPTION OF THE DRAWINGS

The accompanying drawings incorporated herein and forming a part of the specification, illustrate several aspects of the moisture sensor and together with the description serve to explain certain principles of the device. In the drawings.

Reference will now be made in detail to the present preferred embodiment of the moisture sensor, as illustrated in the accompanying drawings.

DETAILED DESCRIPTION SECTION

Figure 1:
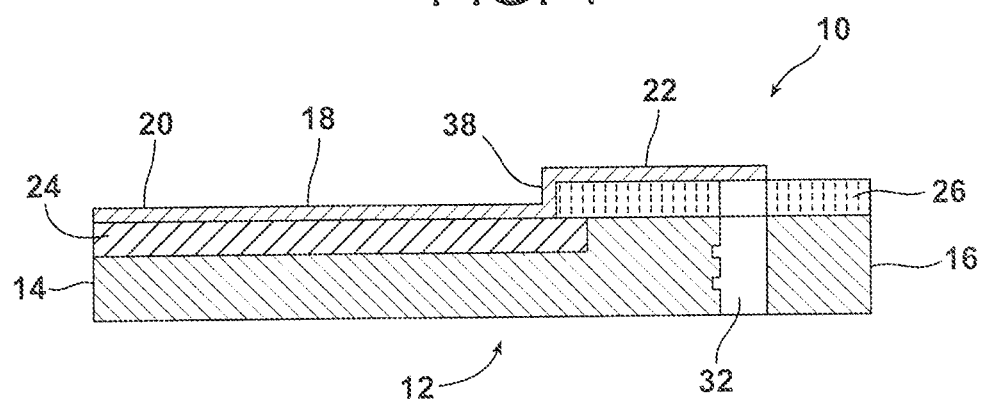
FIG. 1 is a schematic side elevational view of the moisture sensor (leads not shown)
Figure 2:
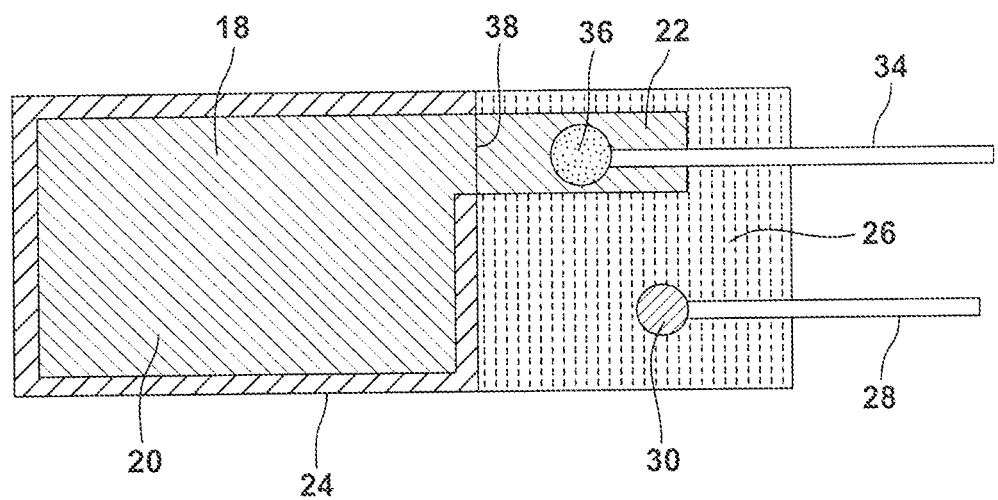
FIG. 2 is a top plan view of the moisture sensor illustrated in FIG. 1.

Reference is now made to FIGS. 1 and 2 illustrating a new and improved moisture sensor 10. The moisture sensor 10 includes a first, bottom or base electrode 12 having a first sensor portion 14 and a first terminal portion 16. The first electrode 12 may or may not include a step as illustrated. The moisture sensor 10 also includes a second or top electrode 18. The second electrode 18 has a second sensor portion 20 and a second terminal portion 22. The second sensor portion 20 overlies and is aligned with the first sensor portion 14 while the second terminal portion 22 overlies and is aligned with the first terminal portion 16. A step-coverage 38 is provided in the second electrode 18 along a transition step line between the second sensor portion 20 and the second terminal portion 22. The transition step line is caused by deposition of a dense insulating material 26 on the conductive substrate (first electrode) 12.

A layer of porous (moisture sensing) dielectric material 24 is provided sandwiched between the first sensor portion 14 and the second sensor portion 20. A layer of dense (non-moisture sensing) insulating material 26 is provided on the first terminal portion 16 and partially sandwiched between the first terminal portion and the second terminal portion 22.

A first lead 28 is connected to the first terminal portion 16 by means of one of the three ways: (1) a conductive fastener such as a conductive screw 30 threadedly received in an aperture 32 formed in the layer of insulating material 26 and the first terminal portion 16 of the first electrode 12; (2) a conductive adhesive 30, where a small portion of the insulating material 26 is etched off to expose the conductive first terminal portion 16 to the conductive adhesive 30 (no aperture 32 is needed in this case); (3) a conductive adhesive 30 directly connected to the first terminal portion 16 from the bottom (no aperture 32 is needed in this case). A second lead 34 is connected to the second terminal portion 22 by means of a conductive adhesive 36. Here it should be noted that the second terminal portion 22 is narrower then the first terminal portion 16 so as to allow the two leads 28, 34 to be properly connected side-by-side on one face of the sensor 10.

In one particular useful embodiment, the first electrode 12 is made from an aluminum substrate, the second electrode 18 is made from a thin gold film, the layer of porous dielectric material 24 is porous alpha-alumina, and the layer of dense insulating material 26 is dense silicon dioxide. It should be appreciated, however, that other materials may utilize to make the sensor 10. For example, the second electrode 18 may be made from a material selected from the group consisting of a conductive metal film, a conductive metal alloy film, a platinum film, a palladium film and a gold/titanium film. The gold/titanium film comprises a gold film deposited upon a very thin titanium layer that promotes adhesion between the gold and the dielectric layer.

The layer of dense insulating material 26 may be made from a material selected from a group consisting of silicon nitride, silicon oxynitride, aluminum oxide, hafnium oxide, hafnium silicon oxide, hafnium silicon oxynitride, silicon dioxide and mixtures thereof.

In the moisture sensor 10, it should be appreciated that the terminal portion 16 of the first electrode 12 is covered with a layer of dense insulating material 26 that serves as a platform for the second terminal portion 22 of the top electrode 18. Because the terminal portion 22 is supported on a layer of dense insulating material 26 instead of a layer of porous dielectric material 24 as is the sensor portion 20, the second lead 34 may be connected to the terminal portion 22 using the conductive adhesive 36 without it adversely affecting the performance of the sensor. This is true as long as the capacitance of the layer of dense insulating material 26 is much less than the base capacitance of the sensor portion consists of a first sensor portion 14, the porous sensing material 24, and a second sensor portion 20 in a dry ambient (<−50° C. dew point). For example, the capacitance of the dense insulating layer 26 should be 10% or less of the base capacitance of the sensor 10. Here it should be appreciated that the thickness of the layer of dense insulating material 26 is important. If it is too thin the layer of dense insulating material 26 may not be able to survive the spark deposition which often is greater than 130V. If it is too thick the second electrode of thin gold film 18 may not be able to cover the side wall of the dense insulating material as necessary to connect the sensor portion 20 with the terminal portion 22. Generally the layer of dense insulating material or dense silicon dioxide 26 should be of a thickness of between about 0.2 μm and about 10.0 μm. In one particularly useful embodiment the layer 26 has a thickness of between about 1.0 μm and about 2.0 μm.

A method of manufacturing the moisture sensor 10 illustrated in FIGS. 1 and 2 may be generally described as follows. The method includes the steps of depositing a layer of dense insulating material 26 on a first terminal portion 16 of a first electrode 12, where the shape and size of the insulating material 26 are defined. This is followed by forming a layer of porous dielectric material 24 on a first sensor portion 14 of the first electrode. Finally a second electrode 18 is deposited over the layer of dense insulating material 26 and the layer of porous dielectric material 24 so as to produce a sensor assembly wherein the second electrode has a second sensor portion 20 overlying the layer of porous dielectric material and a second terminal portion 22 overlying the layer of dense insulating material.

The layer of dense insulating material 26 may be provided on the first terminal portion 16 of the first electrode 12 by any appropriate means including, for example, sputtering. The layer of porous dielectric material 24 may be provided on the first sensor portion 14 of the first electrode 12 by any suitable means including, for example, anodic spark deposition. The second electrode 18 may be deposited over the layer of dense insulating material 26 and layer of porous dielectric material 24 by any appropriate means including, for example, thermal evaporation.

As noted above the first lead 28 may be connected to the first terminal portion 16 by means of a fastener 30 that readily engages an aperture 32 previously drilled or formed in the first or bottom electrode 12. Typically the drilling of the first electrode 12 takes place before providing either layer of dense insulating material or porous dielectric material on that electrode. As also previously noted the second lead 34 is connected to the second terminal portion 22 by a conductive adhesive of a type known in the art such as manufactured by Resinlab LLC of Germantown, Wis. and sold under the Trademark Resinlab SEC1233.

EXAMPLE

An aluminum substrate with a rectangular shape was used. A small hole was drilled on the aluminum substrate, which would be used for the bottom electrode connection. A dense silicon dioxide layer of approximately 1.2-1.5 μm was deposited using RF sputtering on one side of the aluminum substrate. Next anodic spark deposition was carried out to form a porous alpha-alumina layer on the part of the aluminum substrate that was not covered with the dense silicon dioxide. A thin gold film of approximately 50 nm in thickness was then thermally evaporated onto the sensor area (porous alpha-alumina area) as well as the dense silicon dioxide area with a shape as illustrated in FIG. 2. The sensor was then connected with a conductive wire using conductive glue and the bottom electrode was connected to a conductive wire using a small conductive screw.

Currently most solid-state moisture sensors on the market use porous amorphous-or γ-$Al_2O_3$ films, formed by anodization in sulfuric acid solution. These $Al_2O_3$ film sensors exhibit long-term drift of calibration curves. Even the commercial aluminum oxide moisture sensors have to be calibrated twice a year to assure their accuracy and to be stored in a very dry environment. It is very inconvenient for users. It is well known that alpha-alumina or $\alpha$-$Al_2O_3$ (sapphire) is a very stable phase. $\alpha$-$Al_2O_3$ moisture sensors of the type described in detail in this document should have great commercial potential to replace the current $\gamma$-$Al_2O_3$ sensors on the market.

Advantageously the present moisture sensor 10 may be constructed in an inexpensive and cost effective manner, using conductive adhesive for the connection of either or both leads, and may perform reliably for extended periods of time between calibrations. The moisture sensor 10 has a number of applications including but not limited to use of dew point sensors as utilized in dew point measurement instruments. Moisture sensors are also extensively used in industrial processing and environmental control. For example, moisture monitoring is needed for manufacturing of integrated circuits in the semiconductor industry and also has applications in the compressed air industry.

The foregoing description of a preferred embodiment of the moisture sensor 10 has been presented for purposes of illustration and description. The description is not intended to be exhaustive. Obvious modifications or variations of the moisture sensor are possible in light of the above teachings. All such modifications and variations are within the scope of the invention as determined by the appended claims when interpreted in accordance with the breadth to which they are fairly, legally and equitably entitled.

What is claimed:

1. A moisture sensor, comprising;
a first electrode, having a first sensor portion and a first terminal portion;
a layer of porous dielectric material deposited on said first sensor portion;
a layer of dense insulating material deposited on said first terminal portion; and
a second electrode having a second sensor portion and a second terminal portion wherein the second sensor portion is deposited on the porous dielectric material, and the second terminal portion is deposited on the layer of dense insulating material.

2. The sensor of claim 1 further including a first lead connected to said first terminal portion and a second lead connected to said second terminal portion.

3. The sensor of claim 2 wherein said second lead is connected to said second terminal portion by a conductive adhesive.

4. The sensor of claim 3, wherein said first terminal portion includes an aperture and said first lead is connected to said first terminal portion by a fastener secured in said aperture.

5. The sensor of claim 1, wherein said second electrode includes a step between said second sensor portion and said second terminal portion.

6. The sensor of claim 1, wherein said first electrode is made from aluminum.

7. The sensor of claim 1, wherein said second electrode is made from a material selected from a group consisting of a conductive metal film, a conductive metal alloy film, a gold film, a platinum film, a palladium film and a gold/titanium film.

8. The sensor of claim 1, wherein said layer of dielectric material is made from porous alpha-alumina.

9. The sensor of claim 1, wherein said layer of insulating material is made from a material selected from a group consisting of silicon nitride, silicon oxynitride, aluminum oxide, hafnium oxide, hafnium silicon oxide, hafnium silicon oxynitride, silicon dioxide and mixtures thereof.

10. The sensor of claim 1, wherein said first electrode is made of aluminum, said second electrode is made from gold film, said layer of dielectric material is porous alpha alumina and said layer of insulating material is dense silicon dioxide.

11. The sensor of claim 1 wherein said layer of insulating material has a thickness of between about 0.2 µm and about 10.0 µm.

12. The sensor of claim 1 wherein said layer of insulating material has a thickness of between 1.0 µm and about 2.0 µm.

13. A method of manufacturing a moisture sensor comprising:
depositing a layer of insulating material on a first terminal portion of a first electrode;
providing a layer of dielectric material on a first sensor portion of said first electrode;
depositing a second electrode over said layer of insulating material and said layer of dielectric material so as to produce a sensor assembly wherein said second electrode has a second sensor portion overlying said layer of dielectric material and a second terminal portion overlying said layer of insulating material.

14. The method of claim 13 further including connecting a first lead to said first terminal portion and a second lead to said second terminal portion.

15. The method of claim 14, including using a conductive adhesive to connect said second lead to said second terminal portion.

16. The method of claim 15, further including providing an aperture in said first terminal portion before providing said insulating layer on said first terminal portion.

17. The method of claim 16, further including connecting said first lead to said first terminal portion by securing a fastener in said aperture in said first terminal portion.

* * * * *